(12) United States Patent
Krauβ et al.

(10) Patent No.: US 7,920,669 B2
(45) Date of Patent: Apr. 5, 2011

(54) METHODS, APPARATUSES AND COMPUTER READABLE MEDIUMS FOR GENERATING IMAGES BASED ON MULTI-ENERGY COMPUTED TOMOGRAPHY DATA

(75) Inventors: Bernhard Krauβ, Altdorf (DE); Fernando Vega-Higuera, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 286 days.

(21) Appl. No.: 12/010,920

(22) Filed: Jan. 31, 2008

(65) Prior Publication Data
US 2009/0028287 A1    Jan. 29, 2009

Related U.S. Application Data

(60) Provisional application No. 60/961,944, filed on Jul. 25, 2007.

(51) Int. Cl.
*A61B 6/00* (2006.01)
(52) U.S. Cl. ................................ 378/4; 378/5
(58) Field of Classification Search .................. 378/4, 5
See application file for complete search history.

(56) References Cited

U.S. PATENT DOCUMENTS

| | | | |
|---|---|---|---|
| 6,819,735 B2 * | 11/2004 | Bruder et al. ..................... 378/8 |
| 2001/0055016 A1 * | 12/2001 | Krishnan ....................... 345/424 |
| 2002/0028008 A1 * | 3/2002 | Fan et al. ....................... 382/131 |
| 2002/0176619 A1 * | 11/2002 | Love ............................. 382/154 |
| 2002/0183607 A1 * | 12/2002 | Bauch et al. ................... 600/407 |
| 2003/0052875 A1 * | 3/2003 | Salomie ......................... 345/419 |
| 2003/0053697 A1 * | 3/2003 | Aylward et al. ............... 382/203 |
| 2003/0068074 A1 * | 4/2003 | Hahn ............................. 382/128 |
| 2003/0234781 A1 * | 12/2003 | Laidlaw et al. ............... 345/419 |
| 2004/0008809 A1 * | 1/2004 | Webber ............................. 378/8 |
| 2004/0096088 A1 * | 5/2004 | Kohle ............................ 382/128 |
| 2004/0101104 A1 * | 5/2004 | Avinash et al. ............ 378/98.12 |
| 2004/0199064 A1 * | 10/2004 | Van Liere et al. ............. 600/407 |
| 2004/0259065 A1 * | 12/2004 | Geiger .......................... 434/272 |
| 2005/0017972 A1 * | 1/2005 | Poole et al. ................... 345/424 |
| 2005/0074155 A1 * | 4/2005 | Alyassin ....................... 382/131 |

(Continued)

FOREIGN PATENT DOCUMENTS

DE        102006015452 A1     10/2007

OTHER PUBLICATIONS

J. Kniss et al., "Interactive Volume Rendering Using Multi-Dimensional Transfer Functions and Direct Manipulation Widgets", In *Proceedings of IEEE Visualization 2001*, 2001, Scientific Computing and Imaging Institute School of Computing, University of Utah.

(Continued)

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

Methods, apparatuses and computer readable mediums for generating a volume visualization image based on multi-energy computed tomography data are provided. In one method, an image is rendered based on a multi-dimensional graphical representation of the computed tomography data. The computed tomography data includes at least two different energy image data sets and the multi-dimensional graphical representation represents intensity values of each of the at least two different energy image data sets.

45 Claims, 10 Drawing Sheets
(7 of 10 Drawing Sheet(s) Filed in Color)

U.S. PATENT DOCUMENTS

| | | | |
|---|---|---|---|
| 2005/0143654 A1* | 6/2005 | Zuiderveld et al. | 600/443 |
| 2006/0067473 A1* | 3/2006 | Eberhard et al. | 378/98.9 |
| 2007/0217570 A1 | 9/2007 | Grasruck et al. | |
| 2008/0037699 A1 | 2/2008 | Krauss | |

OTHER PUBLICATIONS

Claes Lundström et al., "Local Histograms for Design of Transfer Functions in Direct Volume Rendering", IEEE Transactions on Visualization and Computer Graphics, vol. 12, No. 6, Nov. and Dec. 2006.

Marc Levoy, "Display of Surfaces from Volume Data", IEEE Computer Graphics and Applications 8(3), pp. 29-37, 1988. Computer Science Department, University of North Carolina Chapel Hill.

F. V. Higuera, et al., "Automatic adjustment of Bidimensional Transfer Functions for Direct Volume Visualization of Intracranial Aneurysms," presented at SPIE Medical Imaging: Visualization, Image-guided Procedures, and Display, San Diego, 2004.

Flohr et al.: "First performance evaluation of a dual-source CT (DSCT) system"; Eur Radiol. Feb. 2006;16(2):256-268 Epub Dec. 10, 2010.; Magazine; 2006.

Johnson, Thorsten R.C. et al.; "Material Differentiation by dual energy CT: initial experience"; Eur Radiol. Jun. 2007;17(6), pp. 1510-1517; Others; 2007.

P. Engler et al., "Review of dual-energy computed tomography techniques" Materials Evaluation, vol. 48, May 1990, 623-623, ISSN 0025-5327; Others.

F. Vega-Higuera et al., "High Performance Volume Splatting for Visualization of Neurovascular Data" Proceedings of IEEE Visualization, Oct. 2005, 271-278; Others.

V. Rebuffel and J.-M. Dinten, "Dual-energy X-ray imaging: benefits and limits" Proceedings of European Conference on Non Destructive Testing, 2006; Others; pp. 589-594.

M. Lell et al., "New Techniques in CT Angiography" RadioGraphics RSNA 2006, 45-62, 2006; Others.

C. Heinzl, J. Kastner and E. Gröller, "Surface Extraction from Multi-Material Components for Metrology using Dual Energy CT" IEEE Transactions on Visualization and Computer Graphics, vol. 13, No. 6, Nov./Dec. 2007, 1520-1527; Others.

A. Graser, "Dual Energy CT Characterization of Urinary Calculi: Initial in Vitro and Clinical Experience" Investigative Radiology, 43(2), Feb. 2008, 112-119; Others.

A. Primak et al., "Noninvasive Differentiation of Uric Acid versus Non-Uric Acid Kidney Stones Using Dual-Energy CT" Academic Radiology, vol. 14, No. 12, Dec. 2007, 1441-1447; Others.

H. Scheffel et al., "Dual-Energy Contrast-Enhanced Computed Tomography for the Detection of Urinary Stone Disease" Investigative Radiology, vol. 42, No. 12, 823-829, Dec. 2007; Others.

Gordon Kindlmann et al., "Semi-Automatic Generation of Transfer Functions for Direct Volume Rendering", Program of Computer Graphics, Cornell University (1998).

* cited by examiner

METHODS, APPARATUSES AND COMPUTER READABLE MEDIUMS FOR GENERATING IMAGES BASED ON MULTI-ENERGY COMPUTED TOMOGRAPHY DATA

CROSS REFERENCE TO RELATED APPLICATIONS

This non-provisional U.S. patent application claims priority under 35 U.S.C. §119(e) to provisional application No. 60/961,944 filed on Jul. 25, 2007, the entire contents of which are hereby incorporated herein by reference.

BACKGROUND

In conventional methods of X-ray imaging, attenuation depends on the type of body tissue scanned and the average energy level of the X-ray beam. The average energy level of the X-ray beam may be adjusted via an X-ray tube's energy setting. An X-ray tube's energy setting is measured in kilovolts (kV).

Conventionally, computed tomography (CT) imaging may be performed using a single energy level (referred to as single energy CT imaging) or dual energy levels (referred to as dual energy imaging). Dual energy images may be acquired using two or more scans of different energies during a single procedure or using one or more energy sources.

In conventional dual energy CT imaging, dual image data (e.g., two image data sets or two images) is sometimes referred to as volume data and is obtained using two different energy levels (e.g., 80 kV and 140 kV). Dual image data may be obtained concurrently, simultaneously or sequentially. If two different energy levels are used to acquire dual energy images, each of the two sets of image data may have different attenuation characteristics. The difference in attenuation levels allows for classification of elemental chemical compositions of imaged tissues. In other words, dual-energy CT enables contributions of different X-ray attenuation processes or materials in the CT image to be separated. As a result, standard dual-energy tissue classification techniques perform a so called material analysis or decomposition. The resulting material maps may then be used to perform explicit segmentation of anatomical structures such as osseous tissue in the case of bone removal. In this conventional method of segmentation, however, information about tissue classes included in the scan must be known beforehand in order to choose the appropriate material analysis algorithms.

As an alternative to explicit classification methods, direct volume rendering (DVR) with two dimensional transfer functions (2DTFs) may be used to explore volume data. Direct volume rendering is well known to those of skill in the art, and refers to electronic rendering of a medical image directly from data sets to thereby display visualizations of target regions of the body using multi-dimensional 3D or 4D or more dimensional data. The visualizations may include color as well as internal structures.

DVR does not require the use of intermediate graphic constructs, but may use mathematical models to classify certain structures and may use graphic constructs. Transfer function refers to a mathematical conversion of volume data to color and opacity values used to generate image data.

Conventional 2DTFs are based on data intensities and gradient magnitude for CT data acquired using a single energy level. However, conventional 2DTFs are limited by the intrinsic amount of information that a particular single-energy CT scan provides. More generally, the ability to differentiate tissue classes is restricted by the behavior of x-ray attenuations under one energy level.

SUMMARY OF THE INVENTION

Example embodiments use interactive multi-dimensional transfer functions (MDTFs) based on intensities of multiple energy volumes or data sets (e.g., dual-energy volumes). Editing tools for corresponding MDTFs are coupled with direct volume rendering (DVR) modules for improved visualization and implicit classification of tissues within source data. Additionally, graphics processing unit (GPU) implementation allows interactive adjustment of image parameters such as mixing coefficients, filter settings or the like. Example embodiments provide a framework for interactive exploration of tissue classes in multi-energy scans without preprocessing steps such as explicit material classification.

According to example embodiments source data may include at least two volumes resulting from a multi-energy (e.g., dual energy) scan in which, for example, a first energy level (e.g., about 80 kV) and a second energy level (e.g., about 140 kV) are applied. As a result of the multi-energy scan, source slices are composed of two volumes of identical resolution and voxel size. To display information about tissues contained in the multi-energy dataset, a multi-dimensional histogram is generated.

Example embodiments may also provide automatic histogram partition to create an overview of tissue classes inside the dual-energy data. In addition, example embodiments provide user driven dual-energy implicit tissue classification with DVR and interactive adjustment of the dual-energy transfer function, and GPU based computation of dual-energy mixed images.

At least one example embodiment provides a method for generating a volume visualization image based on multi-energy computed tomography data. In this method, the image is rendered based on a multi-dimensional graphical representation of the computed tomography data. The computed tomography data includes at least two different energy image data sets, wherein the multi-dimensional graphical representation representing intensity values of each of the at least two different energy image data sets.

Another example embodiment provides a method for generating a volume visualization image based on multi-energy computed tomography data. According to this method, the image is generated based on a multi-dimensional transfer function representing selected regions of the computed tomography data. The multi-dimensional transfer function is generated independent of previous tissue classifications associated with the computed tomography data.

Another example embodiment provides a method for generating a volume visualization image based on multi-energy computed tomography data. In this method, the image is generated based on a selected portion of a multi-dimensional graphical representation of the computed tomography data. Each dimension of the multi-dimensional graphical representation is an intensity value associated with one of a plurality of energy levels. At least two of the plurality of energy levels are different.

Another example embodiment provides an apparatus including a graphics processing unit. The graphics processing unit renders an image based on a multi-dimensional graphical representation of computed tomography data. The computed tomography data includes at least two different energy image data sets, and the multi-dimensional graphical representation represents intensity values of each of the at least two different energy image data sets.

Another example embodiment provides an apparatus including a graphics processing unit configured to generate an image based on a multi-dimensional transfer function representing computed tomography data. The multi-dimensional transfer function is generated independent of tissue classifications associated with the computed tomography data.

Another example embodiment provides an apparatus including a graphics processing unit configured to generate an image based on a selected portion of a multi-dimensional graphical representation of computed tomography data. Each dimension of the multi-dimensional graphical representation is an intensity value associated with one of a plurality of energy levels, and at least two of the plurality of energy levels being different.

According to at least some example embodiments, image parameters associated with the image are interactively adjusted to visualize a desired portion of the image. The image parameters include at least one of mixing coefficients and filter settings. A multi-dimensional transfer function is generated based on the multi-dimensional graphical representation. For example, the multi-dimensional transfer function may be generated by selecting a portion of the multi-dimensional graphical representation using a template widget, and computing a transfer function based on the selected portion of the multi-dimensional graphical representation.

According to at least some example embodiments, the at least two image data sets include a first energy image set and a second energy image set, and each of the first and second energy image sets including a plurality of voxels. An image intensity pair for each of the plurality of voxels is identified and the multi-dimensional graphical representation is generated based on the image intensity pair associated with each of the plurality of voxels. The image intensity pairs include a first energy intensity value and second energy intensity value.

The multi-dimensional graphical representation may be generated by calculating, for each image intensity pair, a number of voxels having the same image intensity pair, and assigning colors to the multi-dimensional graphical representation based on the calculated number of voxels for each image intensity pair. The colors are assigned to the multi-dimensional graphical representation based on the calculated number of voxels and a plurality of threshold values.

According to example embodiments, a first image data is obtained using X-rays having a first X-ray energy level and a second image data is obtained using X-rays having a second X-ray energy level. The rendering step renders the image based on the first and second image data.

According to example embodiments, apparatuses may further include a CT unit useable to obtain first image data based on X-rays emitted at a first energy level, and obtain second image data based on X-rays emitted at a second energy level. The image is rendered based on the first and second image data.

The graphics processing unit may further include an editing module to interactively adjust image parameters associated with the image to visualize a desired portion of the image. The editing module may also select a portion of the multi-dimensional graphical representation using a template widget, and the graphics processing unit computes the transfer function based on the selected portion of the multi-dimensional graphical representation.

In example embodiments, the editing tool may also be configured to interactively adjust the generated image by selecting a different portion of the graphical representation of the computed tomography data. In addition, the editing tool may be configured to select a portion of the multi-dimensional graphical representation of the computed tomography data based on desired tissue classifications for evaluation. The selecting of the portion of the multi-dimensional graphical changes the generated image in real-time.

The graphics processing unit further includes a histogram generation module to identify an image intensity pair for each of the plurality of voxels and generate the multi-dimensional graphical representation based on the image intensity pair associated with each of the plurality of voxels. The image intensity pair includes a first energy intensity value and second energy intensity value.

The histogram generation module is further configured to calculate, for each image intensity pair, a number of voxels having the same image intensity pair, and assign colors to the multi-dimensional graphical representation based on the calculated number of voxels for each image intensity pair.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Example embodiments will become more apparent by describing in detail the example embodiments shown in the attached drawings in which.

DETAILED DESCRIPTION OF EXAMPLE EMBODIMENTS

Figure 1:
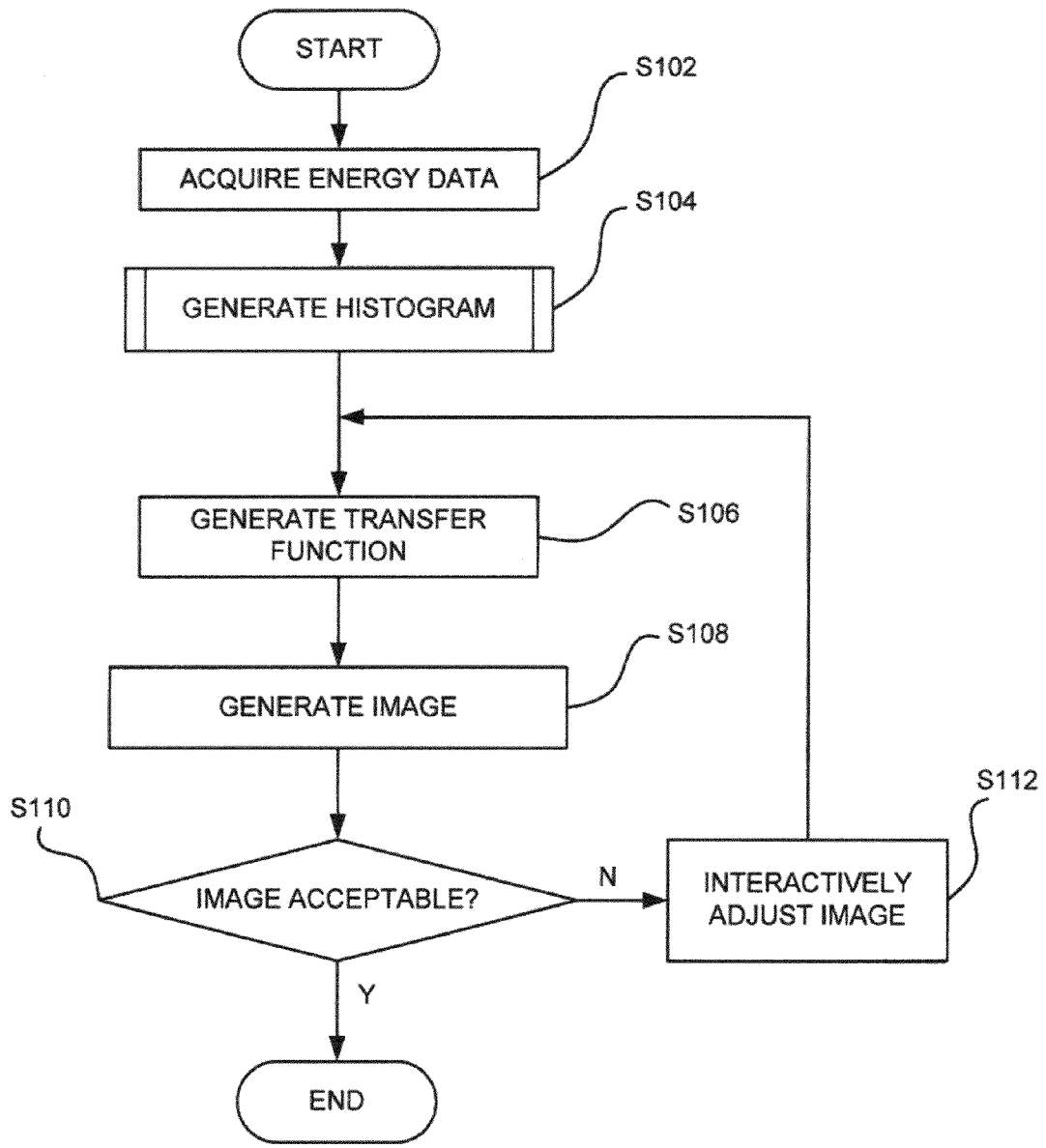
FIG. 1 is a flowchart illustrating a method for generating and interactively adjusting an image according to an example embodiment.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although not required, example embodiments will be described in the general context of computer-executable instructions, such as program modules, being executed by one or more computer processors or CPUs, or one or more graphics processing units (GPUs). Generally, program modules include routines, programs, objects, components, data structures, etc. that perform particular tasks or implement particular abstract data types. The program modules discussed herein may be implemented using existing hardware in existing post-processing workstations. More generally, the program modules discussed herein may be run on post-processing workstations, which may receive input data from one or more CT units (e.g., dual-energy CT units). However, these post-processing workstations may or may not be part of (e.g., integrated with) the CT unit itself.

Example embodiments may also be practiced in distributed computing environments where tasks are performed by remote processing devices that are linked. In a distributed computing environment, program modules may be located in both local and remote memory storage devices.

The acts and symbolic representations of operations described herein may be performed by one or more processors, such as a graphics processing unit (GPU) or the like, unless indicated otherwise. As such, it will be understood that such acts and operations, which are at times referred to as being computer-executed, include the manipulation by the processor of electrical signals representing data in a structured form. This manipulation transforms the data or maintains it at locations in the memory system of the computer, which reconfigures or otherwise alters the operation of the computer in a manner well understood by those skilled in the art.

The data structures where data is maintained are physical locations of the memory that have particular properties defined by the format of the data. However, while example embodiments are described in the foregoing context, it is not meant to be limiting as those of skill in the art will appreciate that various acts and operations described hereinafter may also be implemented in hardware.

Example embodiments provide methods, systems and computer readable mediums (e.g., computer program products) for combining a plurality of image data sets obtained using a plurality of energy levels to generate improved image visualization. As described herein, image information, image data and image data set may be used interchangeably, and may refer to image data used to generate and display a corresponding image to a user. Image, on the other hand, may refer to the image displayed to the user.

Example embodiments provide systems, methods and computer readable mediums for interactive exploration of multi-energy data based on direct volume rendering (DVR) with graphics processing units (GPUs). A multi-dimensional graphical representation (e.g., histogram) of source (e.g., computed tomography) may be displayed (or visualized) such that a user may visually identify tissue classes in the source data. Moreover, a multi-dimensional transfer function (MDTF) editor, editing tool or editing module allows interactive exploration of tissue classes with real time feedback on the corresponding DVR. Thereby, interactive implicit tissue classification with dual energy data is possible.

As described herein, "tissue" refers to blood, cells, bone and the like. "Distinct or different tissue" or "distinct or different material" refers to tissue or material with dissimilar density or other structural or physical characteristics. For example, in medical images, different or distinct tissue or material can refer to tissue having biophysical characteristics different from other (local) tissue. Thus, a blood vessel and spongy bone may have overlapping intensity, but are distinct tissue. In another example, a contrast agent may make tissue have a different density or appearance from blood or other tissue during imaging.

As further described herein, "visualization" refers to presentation or display of medical images to a user (e.g., doctor, clinician, radiologist, etc.) for viewing. The visualization may be in a flat 2-D and/or in 2-D what appears to be 3-D images on a display, data representing features with different visual characteristics such as with differing intensity, opacity, color, texture and the like. The images as presented by the visualization do not have to be the same as the original construct (e.g., they do not have to be the same 2-D slices from the imaging modality).

Figure 2:
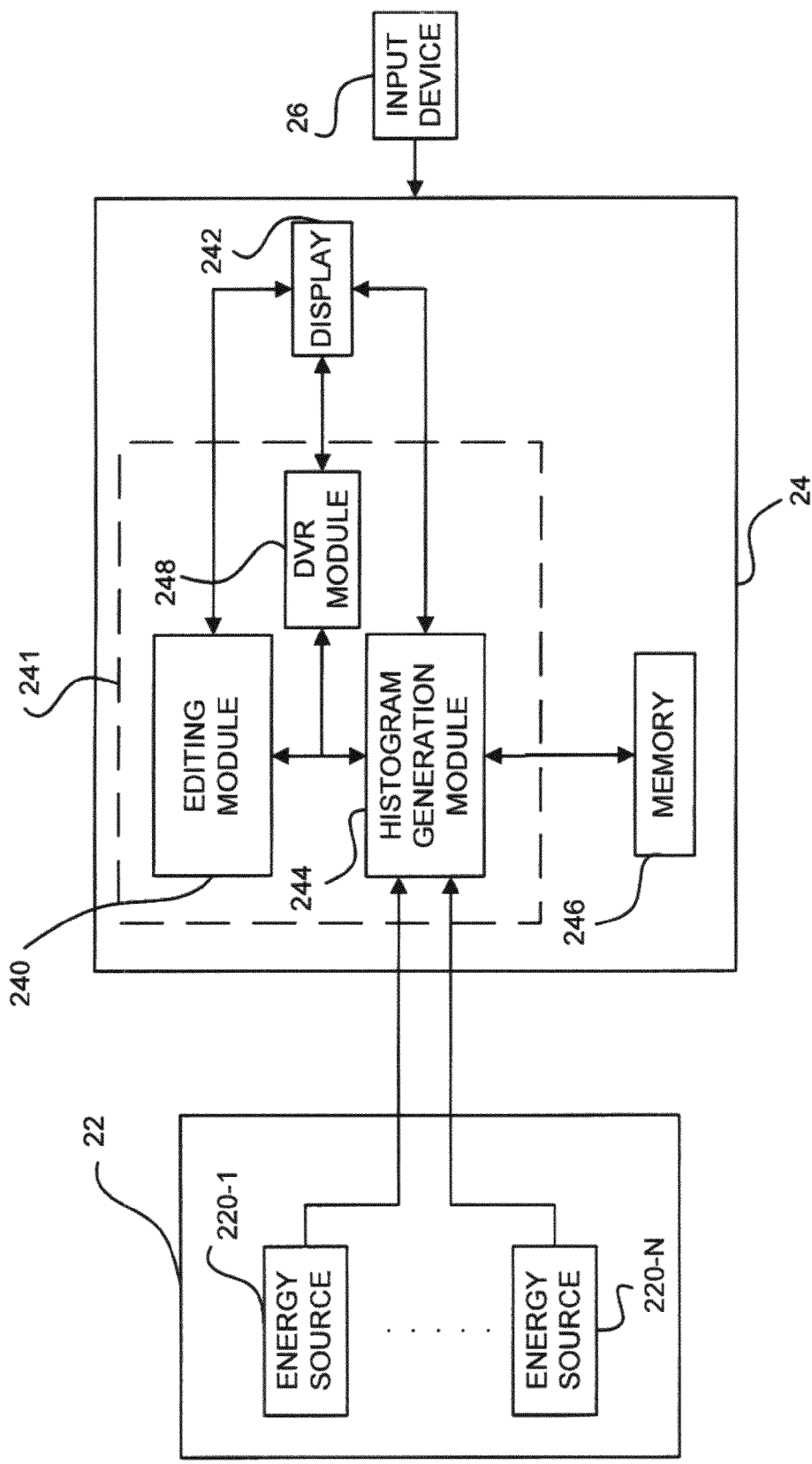
FIG. 2 is a block diagram illustrating a CT system according to an example embodiment.

FIG. 1 is a flowchart illustrating a method for generating and interactively adjusting an image according to an example embodiment. FIG. 2 is a block diagram illustrating a CT system according to an example embodiment. The CT system shown in FIG. 2 may include a dual-energy CT unit 22, which may have similar or substantially similar functionality to CT units well-known in the art. The CT system of FIG. 2 may further include a post-processing workstation 24 having the additional functionality as described herein. Example embodiments will be described with regard FIGS. 1 and 2 collectively. However, it will be understood that methods according to example embodiments may be implemented in conjunction with any suitable CT system.

Although example embodiments will be discussed with regard to being implemented in conjunction with a CT unit and post-processing workstation, example embodiments or at least a portion thereof discussed herein may be implemented on any suitable computer. Such a computer may be completely separate from or integrated with a CT system and/or CT unit. In one example, the methods described herein may be implemented on a conventional personal computer or laptop on which the CT data may be loaded.

Referring to FIGS. 1 and 2, at S102, CT unit (or scanner) 22 may obtain multiple energy data using a plurality of energy sources 220-1-220-N, where N is a natural number. Although FIG. 1 illustrates a plurality of energy sources 220-1-220-N, multiple energy data may be obtained using a single source as is well-known.

Two or more of the energy sources 220-1-220-N may have different X-ray energy levels. In one example embodiment, the CT scanner 22 may include two energy sources 220-1 and 220-2. However, example embodiments are not limited thereto. Because the manner in which dual-energy image data is obtained is well-known, a detailed discussion will be omitted.

The obtained dual energy data may include a plurality of image data sets, each of which may be obtained using a different X-ray energy level. For example purposes, methods according to example embodiments will be described herein with regard to two image data sets obtained using two different X-ray energy sources 220-1 and 220-2 emitting different X-ray energy levels (e.g., about 80 kV and about 140 kV). The energy levels will be referred to herein as first and second energy levels, and the data sets will sometimes be referred to as first energy image data and second energy image data.

In example embodiments described herein, the first and second energy levels may be different. For example, the first energy level may be a lower energy level, such as about 80 kV, whereas the second energy level may be a higher energy level, for example, about 140 kV. Collectively, the first energy image data and the second energy image data may sometimes be referred to as source data.

Within each of the first energy image data and the second energy image data, source slices are composed of two volumes of the same or substantially the same resolution and voxel size. For example, each source slice is composed of voxels generated using the first energy image data and voxels generated using the second energy image data. Each voxel of a slice of source data may sometimes be referred to as a dual-energy voxel.

After being obtained, the dual energy data is loaded onto (e.g., sent to) a post-processing workstation 24. Hereinafter, the post-processing workstation will be referred to as a computer 24. The computer 24 may include a graphics card or graphics processing unit (GPU) 241 capable of generating images based on the dual energy data using direct volume rendering (DVR). As shown in FIG. 2, the GPU 241 may include a histogram generation module 244, an editing module 240 and a DVR module 248. The computer 24 may further include a graphics memory 246 and a display 242. In one example, the loaded dual energy data may be stored as 16-bit luminance textures in graphics memory 246.

Although, FIG. 2 illustrates the histogram generation module 244 as part of the GPU 241, it is not limited thereto. For example, the histogram generation module 244 may be separate from the GPU 241 and configured to generate a histogram as a pre-processing step.

Figure 3:
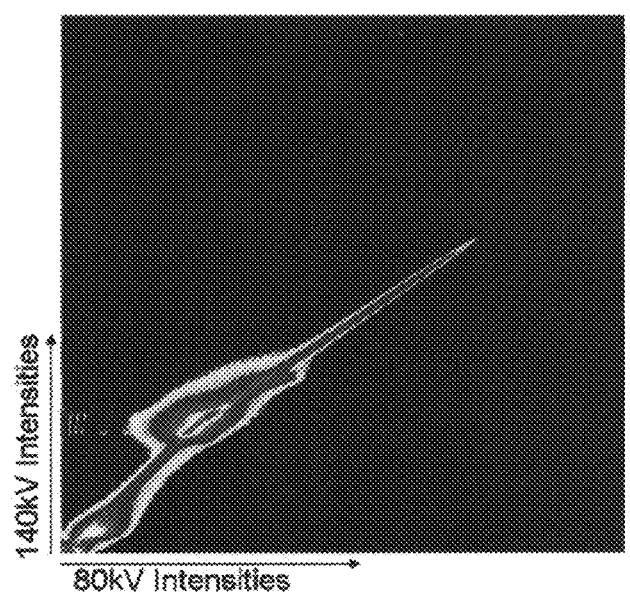
FIG. 3 illustrates an example multi-dimensional histogram according to an example embodiment.

Still referring to FIGS. 1 and 2, at S104 the histogram generation module 244 generates or computes a multi-dimensional graphical representation (e.g., two-dimensional histogram and referred to hereinafter as such) based on the received first and second energy image data. The multi-dimensional histogram displays information about tissues contained in the source data. An example multi-dimensional histogram is shown in FIG. 3. The example histogram shown in FIG. 3 is obtained from a dual-energy head and neck computed tomography angiography (CTA) scan.

Referring to FIG. 3, the multi-dimensional histogram has at least two-dimensions, for example, an x-dimension (represented by the horizontal or x-axis) and a y-dimension (represented by a vertical or y-axis). Each of the x and y dimensions or axes represent image intensities. Because the source data includes image data obtained using two different energy levels (e.g., first energy image data and second energy image data), the source data includes two separate intensities for each voxel v of image data. Hereinafter, the intensity of each voxel v in the first energy image data will be represented by $i_{80}$, where m is the number of the voxel. The intensity of each voxel v in the second energy image data will be represented by $i_{140}$. According to at least one example embodiment, m may be 512.

As briefly described above, in FIG. 3 the x-axis represents intensities of voxels in the first energy image data, whereas the y-axis represents intensities of voxels in the second energy image data. Thus, each voxel v has a first energy intensity value and a second energy intensity value (e.g., referred to as an intensity pair ($i_{80}$, $i_{140}$)), wherein the intensity pair represents a coordinate in the multi-dimensional histogram. Intensities $i_{80}$ and $i_{140}$ may be measured in Hounsfield units, as is well-known in the art.

Figure 4:
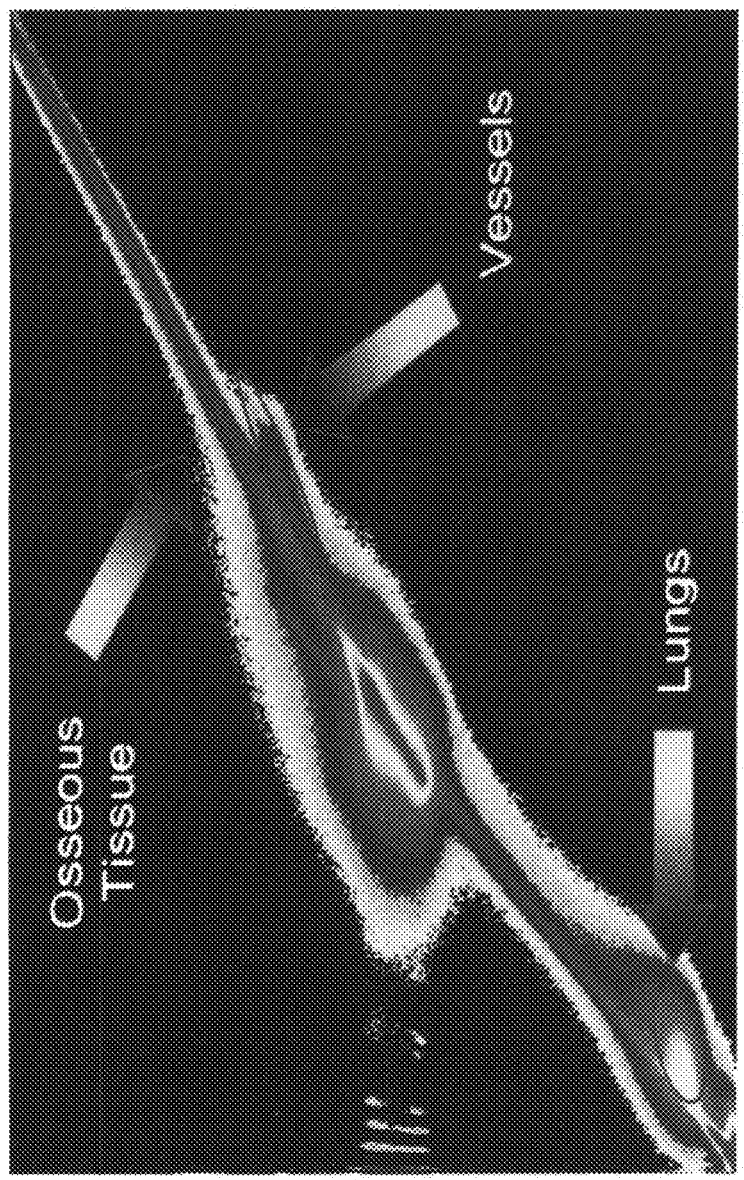
FIG. 4 illustrates an enlarged portion of the histogram shown in FIG. 3.

FIG. 4 illustrates an enlarged portion of the color-annotated histogram shown in FIG. 3. As shown in FIG. 4, the multi-dimensional histogram contains clearly identifiable regions corresponding to, for example, lungs, vessels filled with contrast agent and osseous tissue (each of which is highlighted with an ellipsoid in FIG. 4). Because these tissue classes are clearly visible in the histogram, this information may be used to build a multi-dimensional transfer function (MDTF) for visualizing one or more tissue classes.

Figure 5:
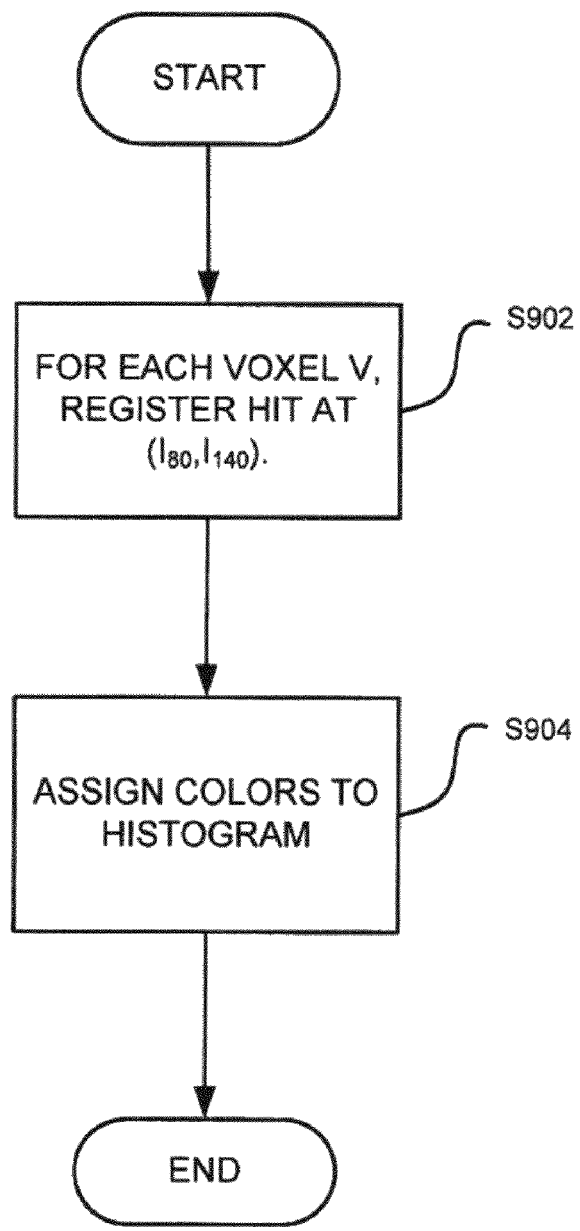
FIG. 5 is a flowchart illustrating a method for generating a multi-dimensional histogram according to an example embodiment.

A method for generating a multi-dimensional histogram (e.g., the histogram shown in FIGS. 3 and 4), according to an example embodiment, is shown in FIG. 5.

Referring to FIG. 5, at step S902, the histogram generation module 244 examines (parses) the source data and registers a 'hit' at coordinate ($i_{80}$, $i_{140}$) for each voxel v of a corresponding 80 kV and 140 kV intensity pair ($i_{80}$, $i_{140}$). The number of hits H for a given intensity pair ($i_{80}$, $i_{140}$) may be stored in graphics memory 246, for example, in association with its corresponding intensity pair ($i_{80}$, $i_{140}$). In one example, the number of hits H and its corresponding intensity pair ($i_{80}$, $i_{140}$) may be stored in a table. As discussed herein, a 'hit' refers to a notation or count that n voxels have an intensity pair ($i_{80}$, $i_{140}$). According to example embodiments, n is an integer.

For example, if the intensity pair ($i_{80}$, $i_{140}$) for a dual-voxel $v_1$ is (200 HU, 250 HU), then a hit is registered for intensity pair (200,250). The intensity pairs and hits are discussed herein as discrete values. Intensity for voxels may be quantized in order to compute the corresponding histogram.

Still referring to FIG. 5, at step S904, the histogram generation module 244 assigns a color to each intensity pair ($i_{80}$, $i_{140}$) having an associated number of hits within a range of threshold values. For example, intensity pairs ($i_{80}$, $i_{140}$) registering a number of hits between a lower bound $THL_{RED}$ and an upper bound $THU_{RED}$ may be assigned the color red.

Similarly, intensity pairs ($i_{80}$, $i_{140}$) registering a number of hits between a lower bound $THL_{GREEN}$ and an upper bound $THU_{GREEN}$ may be assigned the color green.

In another example, intensity pairs ($i_{80}$, $i_{140}$) registering a number of hits between a lower bound $THL_{BLUE}$ and an upper bound $THU_{BLUE}$ may be assigned the color blue.

The upper and lower bounds of the threshold ranges may be determined based on tissue classes and predicted intensity values for given tissue classes. The colors may be associated with the threshold ranges by histogram generation module 244, with or without human operator intervention. A particular number of hits associated with different types of tissue may be known by the user or programmed into the histogram generation module 244.

The histogram generation module 244 determines which range the number of hits falls into and assigns a color as discussed above. This determination and assignment may be performed using a simple lookup table stored in graphics memory 246.

According to example embodiments, the ranges of values associated with each threshold range may overlap. Accordingly, one or more colors may be associated with each intensity pair, and the resultant histogram may show blended combinations of colors, not merely discrete colors. The ranges of values associated with different colors (e.g., red, green, blue, etc.) may overlap, but also may include different values. For example, the ranges of values associated with different colors (e.g., red, green, blue, etc.) may only partially overlap.

Referring back to the example histogram shown in FIGS. 3 and 4, regions with fewer hits are represented in white, while regions with an elevated number of hits may be represented in darker colors such as red, blue, green, etc.

In general, according to example embodiments, colors, but not opacities, are assigned, for pixels in the histogram according to the number of hits of particular histogram positions.

The histogram (e.g., as shown in FIGS. 3 and 4) generated by the histogram generation module 244 may be displayed to a user via display 242. Visualization of the multi-dimensional histogram allows for easier identification of tissue classes within the source data.

In another example embodiment, a multi-dimensional histogram image may be generated using a standard segmentation algorithm such as split and merge, and then assigning different colors to individual regions of the 2DTF created over the histogram.

Returning to FIGS. 1 and 2, as noted above, the generated histogram may be displayed to a user. At step S106, the computer 24 may generate a multi-dimensional transfer function based on the generated multi-dimensional histogram. In one example, the multi-dimensional histogram may be displayed to a user via the display 242, and the user may select at least one portion of the multi-dimensional histogram using an interactive template widget via editing module (editing tool) 240. The editing tool 240 may be an editing tool such as described by Kniss et al., "Interactive Volume Rendering Using Multi-Dimensional Transfer Functions and Direct Manipulation Widgets", In Proceedings of IEEE Visualization 2001, (2001). Because editing tools including template widgets such as this are well-known, a detailed discussion will be omitted.

Using the editing tool 240 and input device 26 (e.g., a mouse, keyboard, etc.), the user may select different portions of the multi-dimensional histogram using an interactive template widget. The selecting of different portions of the histogram results in generation of a transfer function for the widget, which is suitable for generating an image using direct volume rendering (DVR).

Figure 6:
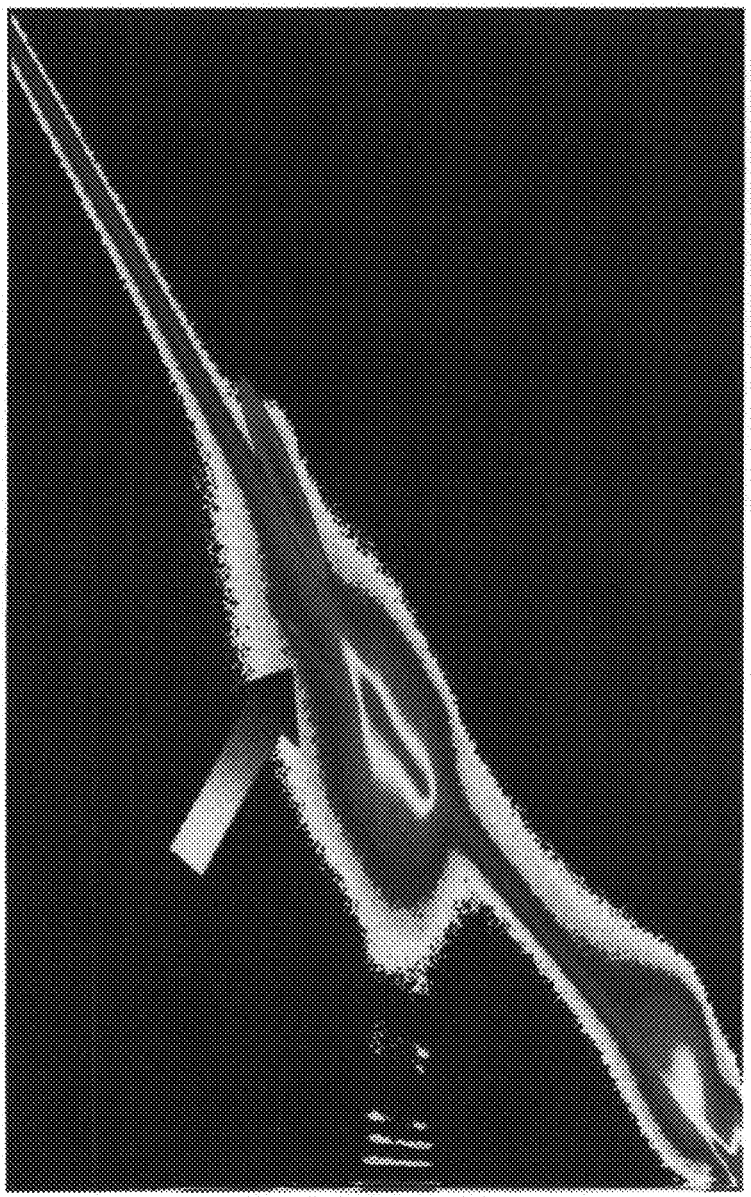
FIG. 6 illustrates an example histogram in which a portion is selected using an ellipsoid template widget.

Referring back to FIGS. 3 and 4, for example, if the user desires to view only vessels of the body, the user may select the portion of histogram labeled "vessels," to generate a transfer function that results in an image showing only vessels. An example histogram with a selected portion is shown in FIG. 6. As shown, the widget may be in the form of an ellipsoid.

The generated transfer function may be stored as one-dimensional and/or two-dimensional RGBA textures in graphics memory 246 and provided to the DVR module 248. As is well-known in the art, RGBA refers to a 4-dimensional array storing red, green and blue intensities and opacity, which is referred to as an alpha value. In example embodiments, the transfer function may be stored in the graphics memory 246, and obtained by the DVR module 248 via a read operation. The transfer function may be obtained by rendering user created (or template widgets) on a graphics memory buffer. This memory buffer is used as a source for the RGBA texture. The RGBA texture serves as a look-up table for tissue classification. According to example embodiments, the look-up table may constitute the transfer function.

At step S108, the DVR module 248 generates an image using direct volume rendering (DVR) based on the generated transfer function. The image is displayed to the user via display 242. The DVR module 248 may perform volume rendering using standard volume slicing using dual energy data for texturing view aligned polygons. Because methods for generating DVR images based on multi-dimensional transfer functions obtained from multi-dimensional histograms (e.g., the above-described volume rendering) is well-known in the art, a detailed discussion will be omitted for the sake of brevity. Although a volume slicing bricker approach is described above, other algorithms such as GPU based ray casting may also be used in connection with example embodiments.

Figure 7:
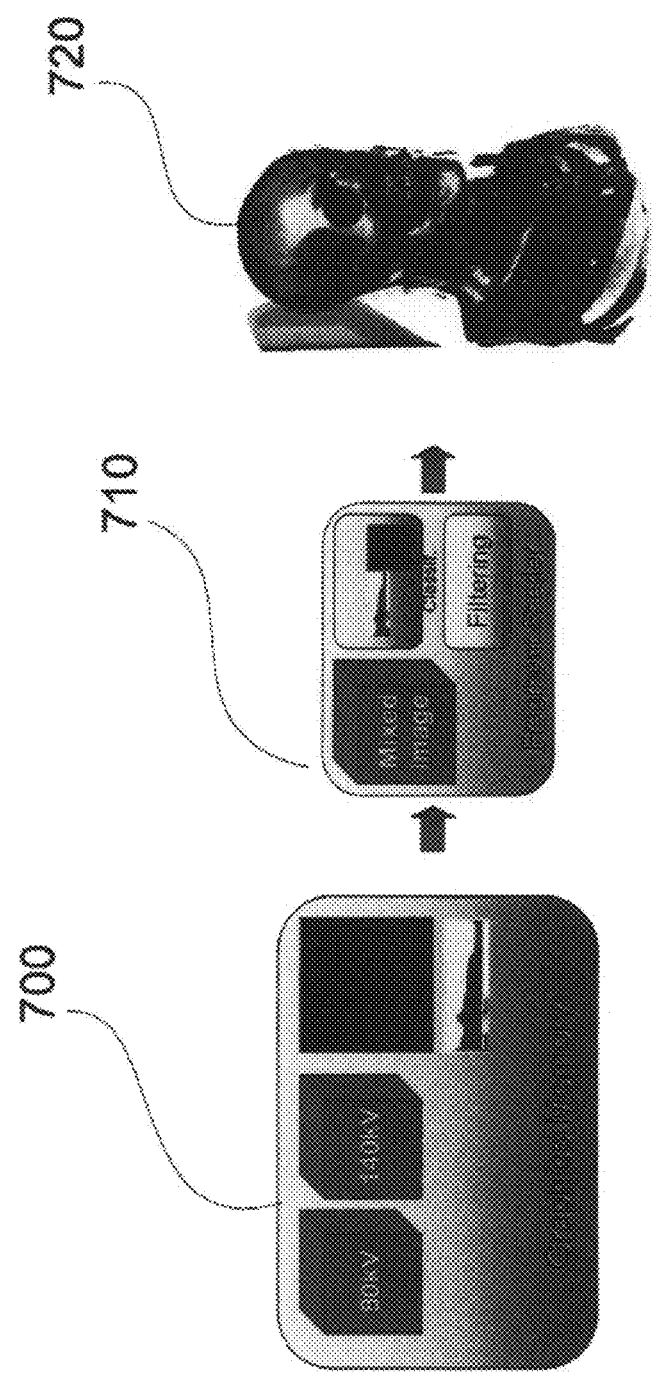
FIG. 7 shows a shader program for computing mixed image, noise filtering, tissue classification and local illumination in real time.

According to example embodiments, the above-discussed methods (e.g., including generating the mixed image, noise filtering, tissue classification and local illumination) may be computed in real-time in a shader program such as shown in FIG. 7. As a result, interactive frame rates are obtained and changes to the transfer functions are updated in real time. At least this example embodiment is independent of the volume rendering approach.

In more detail, as shown in FIG. 7, the graphics memory 700 may store volumes of dual-energy data (e.g., 80 kV and 140 KV image data), and 1-D and 2-D RGBA textures. Fragment shader program 720 may generate a mixed image based on the stored dual-energy image data, perform tissue classification and perform filtering to generate the resultant dual energy image 730. As is well-known in the art, a fragment shader program refers to software executed on a GPU, and is analogous to a computer program executed on a conventional processor or CPU. The fragment shader program 720 may perform the above-discussed functions/operations on-the-fly in real-time.

At step S110, the user decides if the image generated is acceptable. If the user determines that the image is acceptable, the process terminates. However, if the user determines that the image is unacceptable, the user may interactively adjust the DVR image in real-time using input device 26. For example, the user may make real-time fine adjustments to the image by moving the above widget relatively slightly using a mouse input device. On the other hand, the user may view an entirely different tissue class by selecting a different portion of the histogram. For example, if the user desires to view Osseous tissue, the user may select the portion of the histogram labeled "Osseous Tissue."

The user may interactively adjust the displayed image using the editing tool and the input device 26. For example, the user may move the above-discussed template widget throughout the multi-dimensional histogram and the DVR image may be modified in response to the movement in real-time. The editing tool allows the user to interactively and adaptively adjust the transfer function used in generating the DVR image by selecting different portions of the multi-dimensional histogram.

According to example embodiments, different portions of the multi-dimensional histogram may be selected by interactively moving a transfer function template widget over a target region in the multi-dimensional histogram as shown, for example, in FIG. 6. As the transfer function template widget is moved, the corresponding DVR image is updated in real time, such that the user may finely adjust the DVR image to obtain optimal visualizations. Accordingly, implicit segmentation of different tissue classes may be performed.

In addition to the above-discussed adjustments, the user may interactively adjust image parameters such as mixing coefficients and filter settings used in blending dual-energy data to generate a mixed energy image. In one example, a mixing co-efficient may be the alpha ($\alpha$) factor in the following equation used in generating mixed dual-energy images:

$$M = I_{80}\alpha + I_{140}(1-\alpha).$$

In the above equation, M represents the mixed energy image, $I_{80}$ represents first energy image data (e.g., 80 kV image data) and $I_{140}$ represents second energy image data (e.g., 140 kV image data).

According to at least some example embodiments, the multi-dimensional transfer function may be generated independent of previous tissue classifications associated with the computed tomography data in that information about tissue classes included in the scan does not need to be known beforehand and/or tissue classifications may be interactively adjusted on-the-fly in real-time using template widgets.

A more specific example of this interactive adjustment will be described in more detail below with regard to FIGS. 8 and 9.

Figure 8:
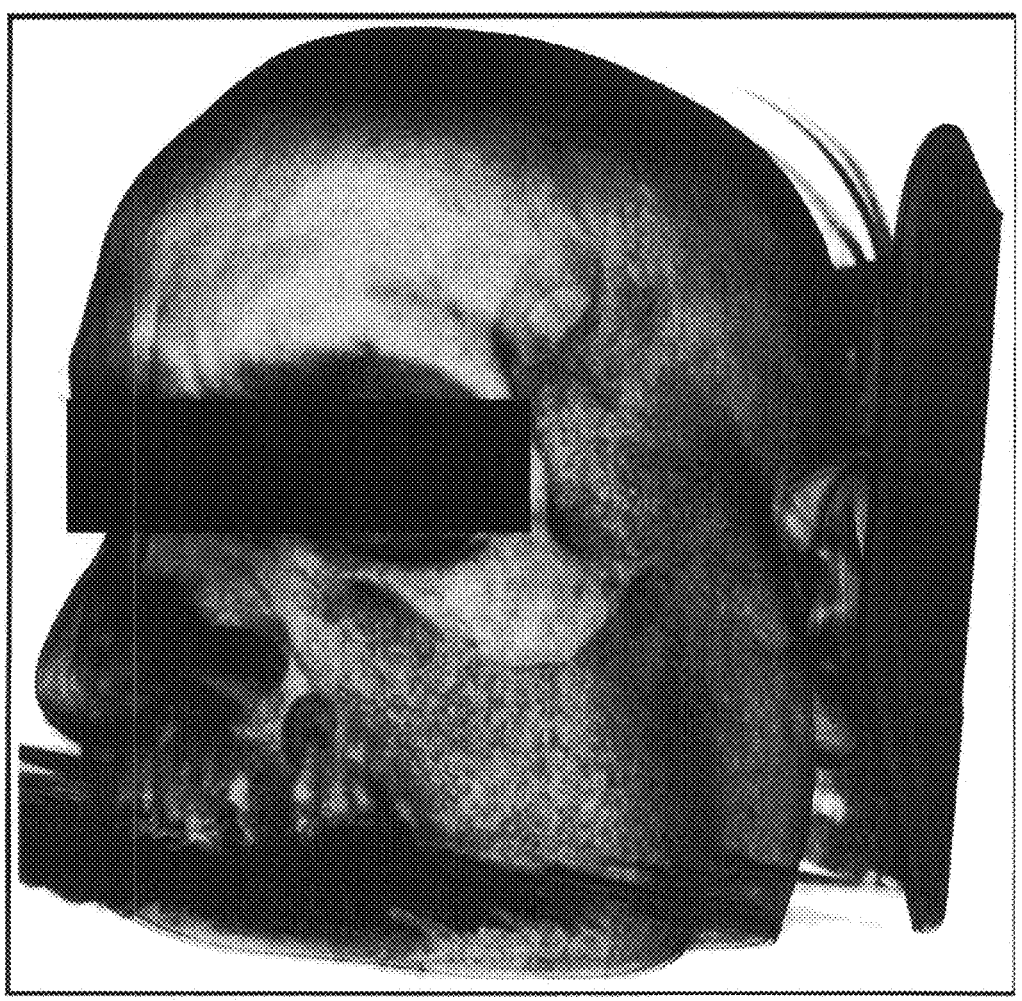
FIG. 8 shows an image generated using a standard DVR of a mixed image.

FIG. 8 shows an image generated using a standard DVR of the mixed image, which is well-known in the art. FIG. 9 shows vessel visualization with dual-energy, in which the user has selected, for example, the portion of histogram labeled "Vessels," in FIG. 4.

Figure 9:
FIG. 9 shows vessel visualization with dual-energy, in which the user has selected the portion of histogram labeled "Vessels," in FIG. 4.

Referring to FIGS. 8 and 9, according to example embodiments, contrary to visualization with standard LDTF only, structures that disturb vessel display such as head support and osseous tissues are not displayed, because these tissue classes do not overlap in the multi-dimensional histogram. Additionally, the boundary between osseous tissue and vessels is smoothly reconstructed. In one example, carotid arteries through the skull base and venous sinus around the skull are rendered without the typical staircase artifacts from explicit segmentation methods.

As an alternative to assigning colors directly to the multi-dimensional transfer function, a combined single dimension transfer function/multi-dimensional transfer function (e.g., 1DTF/2DTF) approach may be applied. In this example embodiment, colors and opacities may be assigned by adjusting a single-dimensional transfer function for the mixed image. The editing tool is used for creating a binary mask that is then applied to determine visibility of voxels in the visualization as shown in FIG. 10.

Figure 10:
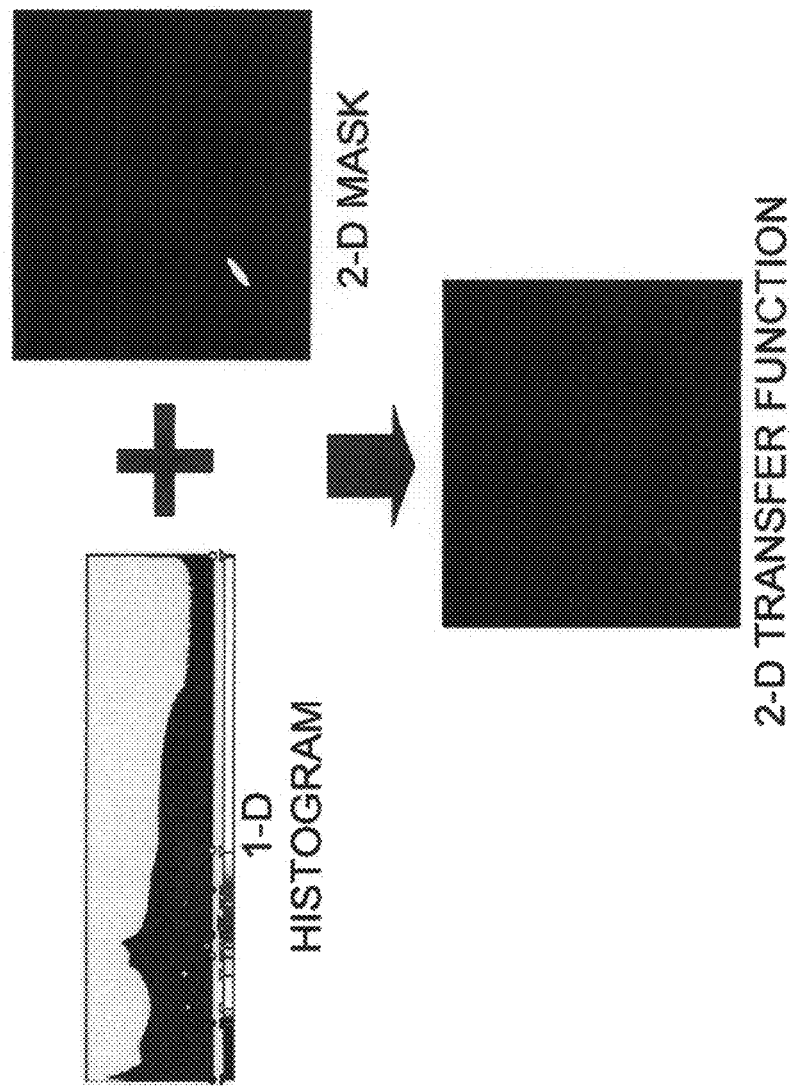
FIG. 10 illustrates another implementation of example embodiments.

In FIG. 10, contrary to extracting an RGBA image from the user adjusted widgets as described above, in this example embodiment only the alpha image is extracted. The resulting two dimensional image is then used to mask voxels given their dual-energy intensity. If the dual-energy intensity pair of a particular voxel is inside the mask, the voxel is rendered. Colors are assigned based on the mixed image intensity for this given voxel according to a 1DTF obtained with well-known methods.

Example embodiments may also be implemented, in software, for example, as any suitable computer program. For example, a program in accordance with one or more example embodiments of the present invention may be a computer program product causing a computer to execute one or more of the example methods described herein: a method for determining a parameter in a system for implementing a future clinical study.

The computer program product may include a computer-readable medium having computer program logic or code portions embodied thereon for enabling a processor of the apparatus to perform one or more functions in accordance with one or more of the example methodologies described above. The computer program logic may thus cause the processor to perform one or more of the example methodologies, or one or more functions of a given methodology described herein.

The computer-readable medium may be a built-in medium installed inside a computer main body or removable medium arranged so that it can be separated from the computer main body. Examples of the built-in medium include, but are not limited to, rewriteable non-volatile memories, such as RAMs, ROMs, flash memories, and hard disks. Examples of a removable medium may include, but are not limited to, optical storage media such as CD-ROMs and DVDs; magneto-optical storage media such as MOs; magnetism storage media such as floppy disks (trademark), cassette tapes, and removable hard disks; media with a built-in rewriteable non-volatile memory such as memory cards; and media with a built-in ROM, such as ROM cassettes.

These programs may also be provided in the form of an externally supplied propagated signal and/or a computer data signal (e.g., wireless or terrestrial) embodied in a carrier wave. The computer data signal embodying one or more instructions or functions of an example methodology may be carried on a carrier wave for transmission and/or reception by an entity that executes the instructions or functions of the example methodology. For example, the functions or instructions of the example embodiments may be implemented by processing one or more code segments of the carrier wave, for example, in a computer, where instructions or functions may be executed for determining a parameter in a system for implementing a future clinical study, in accordance with example embodiments described herein.

Further, such programs, when recorded on computer-readable storage media, may be readily stored and distributed. The storage medium, as it is read by a computer, may enable the methods and/or apparatuses, in accordance with the example embodiments described herein.

Example embodiments being thus described, it will be obvious that the same may be varied in many ways. For example, the methods according to example embodiments of the present invention may be implemented in hardware and/or software. The hardware/software implementations may include a combination of processor(s) and article(s) of manufacture. The article(s) of manufacture may further include storage media and executable computer program(s), for example, a computer program product stored on a computer readable medium.

The executable computer program(s) may include the instructions to perform the described operations or functions. The computer executable program(s) may also be provided as part of externally supplied propagated signal(s). Such variations are not to be regarded as departure from the spirit and scope of the example embodiments, and all such modifications as would be obvious to one skilled in the art are intended to be included within the scope of the following claims.

The invention being thus described, it will be obvious that the same may be varied in many ways. Such variations are not to be regarded as a departure from the invention, and all such modifications are intended to be included within the scope of the invention.

We claim:

1. A method for generating a volume visualization image based on multi-energy computed tomography data, the method comprising:
   rendering, by a graphics processing apparatus, the image based on a multi-dimensional graphical representation of the computed tomography data, the computed tomography data including at least two different energy image data sets, the multi-dimensional graphical representation representing intensity values of each of the at least two different energy image data sets; wherein
   each dimension of the multi-dimensional graphical representation represents intensity values for a different energy level.

2. The method of claim 1, further comprising:
   interactively adjusting image parameters associated with the rendered image to visualize a desired portion of the image.

3. The method of claim 2, wherein the image parameters include at least one of mixing coefficients and filter settings.

4. The method of claim 2, further comprising:
   generating the multi-dimensional transfer function based on the multi-dimensional graphical representation.

5. The method of claim 4, wherein the generating further comprises:
   selecting a portion of the multi-dimensional graphical representation using a template widget; and
   computing a transfer function based on the selected portion of the multi-dimensional graphical representation.

6. The method of claim 2, wherein the interactively adjusting further comprises:
   selecting a portion of a multi-dimensional transfer function associated with the rendered image to adjust the image parameters.

7. The method of claim 1, wherein the at least two image data sets includes a first energy image set and a second energy image set, each of the first and second energy image sets including a plurality of voxels, the method further comprising:
   identifying an image intensity pair for each of the plurality of voxels, the image intensity pair including a first energy intensity value and second energy intensity value; and
   generating the multi-dimensional graphical representation based on the image intensity pair associated with each of the plurality of voxels.

8. The method of claim 7, wherein the generating further comprises:
   calculating, for each image intensity pair, a number of voxels having the same image intensity pair; and
   assigning colors to the multi-dimensional graphical representation based on the calculated number of voxels for each image intensity pair.

9. The method of claim 8, wherein the colors are assigned to the multi-dimensional graphical representation based on the calculated number of voxels and a plurality of threshold values.

10. The method of claim 1, further comprising:
    obtaining first image data using X-rays having a first X-ray energy level; and
    obtaining second image data using X-rays having a second X-ray energy level; wherein
    the rendering renders the image based on the first and second image data.

11. A computer readable medium storing computer executable instructions that when executed cause a computer to perform the method of claim 1.

12. The method of claim 1, wherein the multi-dimensional graphical representation is a multi-dimensional histogram.

13. A method for generating a volume visualization image based on multi-energy computed tomography data, the method comprising:
    generating, by a graphics processing apparatus, the image based on a multi-dimensional transfer function representing selected regions of the computed tomography data, the multi-dimensional transfer function being generated independent of previous tissue classifications associated with the computed tomography data; wherein
    each dimension of the multi-dimensional transfer function represents intensity values for a different energy level.

14. A computer readable medium storing computer executable instructions that when executed cause a computer to perform the method of claim 13.

15. The method of claim 13, wherein the multi-dimensional transfer function is a multi-dimensional histogram.

16. A method for generating a volume visualization image based on multi-energy computed tomography data, the method comprising:
    generating, by a graphics processing apparatus, the image based on a selected portion of a multi-dimensional graphical representation of the computed tomography data, each dimension of the multi-dimensional graphical representation representing intensity values associated with a different one of a plurality of energy levels.

17. The method of claim 16, further comprising:
    interactively adjusting the generated image by selecting a different portion of the graphical representation of the computed tomography data.

18. The method of claim 16, further comprising:
    selecting a portion of the multi-dimensional graphical representation of the computed tomography data based on desired tissue classifications for evaluation, wherein
    the selecting of the portion of the multi-dimensional graphical changes the generated image in real-time.

19. The method of claim 16, further comprising:
    computing the multi-dimensional transfer function based on the selected portion of the multi-dimensional graphical representation; and wherein
    the generating generates the image based on the computed multi-dimensional transfer function.

20. The method of claim 16, further comprising:
    obtaining first image data using X-rays having a first X-ray energy level;
    obtaining second image data using X-rays having a second X-ray energy level; and wherein generating the multi-dimensional graphical representation based on the obtained first and second image data.

21. A computer readable medium storing computer executable instructions that when executed cause a computer to perform the method of claim 16.

22. The method of claim 16, wherein the multi-dimensional graphical representation is a multi-dimensional histogram.

23. An apparatus comprising:
a graphics processing unit to render an image based on a multi-dimensional graphical representation of computed tomography data, the computed tomography data including at least two different energy image data sets, the multi-dimensional graphical representation representing intensity values of each of the at least two different energy image data sets; wherein
each dimension of the multi-dimensional graphical representation represents intensity values for a different energy level.

24. The apparatus of claim 23, further comprising:
a CT unit useable to,
obtain first image data based on X-rays emitted at a first energy level, and
obtain second image data based on X-rays emitted at a second energy level, wherein
the image is rendered based on the first and second image data.

25. The apparatus of claim 23, wherein the graphics processing unit comprises:
an editing module to interactively adjust image parameters associated with the image to visualize a desired portion of the image.

26. The apparatus of claim 25, wherein the image parameters include at least one of mixing coefficients and filter settings.

27. The apparatus of claim 25, wherein the editing module enables a user to select a portion of a multi-dimensional transfer function associated with the rendered image to adjust the image parameters thereby interactively adjusting the image.

28. The apparatus of claim 23, wherein the graphics processing unit is further configured to generate a multi-dimensional transfer function based on the multi-dimensional graphical representation.

29. The apparatus of claim 28, wherein the graphics processing unit comprises:
an editing module to select a portion of the multi-dimensional graphical representation using a template widget; and wherein
the graphics processing unit computes the transfer function based on the selected portion of the multi-dimensional graphical representation.

30. The apparatus of claim 23, wherein the at least two image data sets includes a first energy image set and a second energy image set, each of the first and second energy image sets including a plurality of voxels, the graphics processing unit comprising:
a histogram generation module to identify an image intensity pair for each of the plurality of voxels, the image intensity pair including a first energy intensity value and second energy intensity value, and generate the multi-dimensional graphical representation based on the image intensity pair associated with each of the plurality of voxels.

31. The apparatus of claim 30, wherein the histogram generation module is further configured to calculate, for each image intensity pair, a number of voxels having the same image intensity pair, and assign colors to the multi-dimensional graphical representation based on the calculated number of voxels for each image intensity pair.

32. The apparatus of claim 31, wherein the colors are assigned to the multi-dimensional graphical representation based on the calculated number of voxels and a plurality of threshold values.

33. The apparatus of claim 23, wherein the multi-dimensional graphical representation is a multi-dimensional histogram.

34. An apparatus comprising:
a graphics processing unit to generate an image based on a multi-dimensional transfer function representing computed tomography data, the multi-dimensional transfer function being generated independent of tissue classifications associated with the computed tomography data: wherein
each dimension of the multi-dimensional transfer function represents intensity values for a different energy level.

35. The apparatus of claim 34, wherein the graphics processing unit comprises:
an editing tool to interactively adjust the generated image by selecting different portions of the graphical representation of the computed tomography data.

36. The apparatus of claim 34, wherein the graphics processing unit comprises:
an editing tool to select a portion of the multi-dimensional graphical representation of the computed tomography data based on desired tissue classifications for evaluation, wherein
the selecting of the portion of the multi-dimensional graphical changes the generated image in real-time.

37. The apparatus of claim 4, wherein the graphics processing unit is further configured to compute a multi-dimensional transfer function based on a selected portion of the multi-dimensional graphical representation, and generate the image based on the computed multi-dimensional transfer function.

38. The apparatus of claim 34, further comprising:
a CT unit useable to,
obtain first image data based on X-rays emitted at a first energy level, and
obtain second image data based on X-rays emitted at a second energy level, wherein
the graphics processing unit generates the multi-dimensional graphical representation based on the obtained first and second image data.

39. The apparatus of claim 34, wherein the multi-dimensional transfer function is a multi-dimensional histogram.

40. An apparatus comprising:
a graphics processing unit to generate an image based on a selected portion of a multi-dimensional graphical representation of computed tomography data, each dimension of the multi-dimensional graphical representation representing intensity values associated with a different one of a plurality of energy levels.

41. The apparatus of claim 40, wherein the graphics processing unit comprises:
an editing tool to interactively adjust the generated image by selecting a different portion of the graphical representation of the computed tomography data.

42. The apparatus of claim 40, wherein the graphics processing unit comprises:
an editing tool to select a portion of the multi-dimensional graphical representation of the computed tomography data based on desired tissue classifications for evaluation, wherein
the selecting of the portion of the multi-dimensional graphical changes the generated image in real-time.

43. The apparatus of claim 40, wherein the graphics processing unit is further configured to compute a multi-dimensional transfer function based on the selected portion of the multi-dimensional graphical representation, and generate the image based on the computed multi-dimensional transfer function.

44. The apparatus of claim 40, further comprising:
a CT unit useable to,
obtain first image data based on X-rays emitted at a first energy level, and
obtain second image data based on X-rays emitted at a second energy level, wherein
the graphics processing unit generates the multi-dimensional graphical representation based on the obtained first and second image data.

45. The apparatus of claim 40, wherein the multi-dimensional graphical representation is a multi-dimensional histogram.

* * * * *